US011406774B2

(12) United States Patent
Trzecieski

(10) Patent No.: US 11,406,774 B2
(45) Date of Patent: *Aug. 9, 2022

(54) AROMATHERAPY VAPORIZATION DEVICE

(71) Applicant: GS Holistic, LLC, Los Angeles, CA (US)

(72) Inventor: Michael Alexander Trzecieski, Toronto (CA)

(73) Assignee: GS Holistic, LLC, Los Angeles, CA (US)

( * ) Notice: Subject to any disclaimer, the term of this patent is extended or adjusted under 35 U.S.C. 154(b) by 28 days.

This patent is subject to a terminal disclaimer.

(21) Appl. No.: 16/880,225

(22) Filed: May 21, 2020

(65) Prior Publication Data

US 2021/0038835 A1 Feb. 11, 2021

Related U.S. Application Data

(63) Continuation of application No. 15/372,308, filed on Dec. 7, 2016, now Pat. No. 10,695,510.

(60) Provisional application No. 62/263,751, filed on Dec. 7, 2015.

(51) Int. Cl.
| *A61M 11/04* | (2006.01) |
| *A61M 15/00* | (2006.01) |
| *A61L 9/03* | (2006.01) |
| *A61L 9/14* | (2006.01) |

(52) U.S. Cl.
CPC ............. *A61M 11/042* (2014.02); *A61L 9/03* (2013.01); *A61L 9/14* (2013.01); *A61M 15/0021* (2014.02); *A61L 2209/11* (2013.01); *A61L 2209/135* (2013.01); *A61M 15/0015* (2014.02); *A61M 2205/3368* (2013.01); *A61M 2205/502* (2013.01); *A61M 2205/8206* (2013.01)

(58) Field of Classification Search
CPC .................................................... A61M 11/042
See application file for complete search history.

(56) References Cited

U.S. PATENT DOCUMENTS

| 4,966,239 A | 10/1990 | Hutchison |
| 5,269,379 A | 12/1993 | Millar et al. |
| 6,112,680 A | 9/2000 | Hummer |
| 6,527,502 B2 | 3/2003 | Leijenaar |
| 6,779,610 B2 | 8/2004 | Brouwer et al. |
| 7,066,277 B2 | 6/2006 | Hendriks et al. |
| 7,070,004 B2 | 7/2006 | Hendriks et al. |
| 7,096,967 B2 | 8/2006 | Pohlman, Jr. et al. |
| 8,196,982 B1 | 6/2012 | Crunkelton |
| 8,813,861 B2 | 8/2014 | Stefanski et al. |
| 10,743,479 B2 | 8/2020 | Brouwer et al. |

(Continued)

*Primary Examiner* — Jenna Zhang
(74) *Attorney, Agent, or Firm* — Kevin Schraven; Anooj Patel; Hankin Patent Law, APC

(57) ABSTRACT

A novel aromatherapy vaporization device is disclosed having a first and second housing with a heating chamber for receiving of phyto material. The heating chamber has an ambient air input port that receives ambient air that does not flow past hot electrical components when entering the heating chamber. An inhalation tube is coupled with the heating chamber for receiving of phyto material vapor therein in a second mode of operation and in a first mode of operation the inhalation tube is uncoupled from the heating chamber to allow for loading of phyto material therein.

20 Claims, 7 Drawing Sheets

(56) References Cited

U.S. PATENT DOCUMENTS

| | | | |
|---|---|---|---|
| 2004/0009245 A1* | 1/2004 | Vail, III | A61M 15/00 |
| | | | 424/742 |
| 2004/0188107 A1 | 9/2004 | Hendriks et al. | |
| 2005/0000705 A1 | 1/2005 | Brouwer et al. | |
| 2005/0167123 A1 | 8/2005 | Pohlman et al. | |
| 2007/0045288 A1* | 3/2007 | Nelson | A61M 11/041 |
| | | | 219/533 |
| 2008/0216824 A1* | 9/2008 | Ooida | A61M 16/161 |
| | | | 128/200.21 |
| 2013/0247910 A1* | 9/2013 | Postma | A61M 15/0023 |
| | | | 128/203.26 |
| 2013/0298905 A1* | 11/2013 | Levin | A24F 40/90 |
| | | | 128/202.21 |
| 2016/0015309 A1* | 1/2016 | Mills | A61B 5/7282 |
| | | | 600/303 |

* cited by examiner

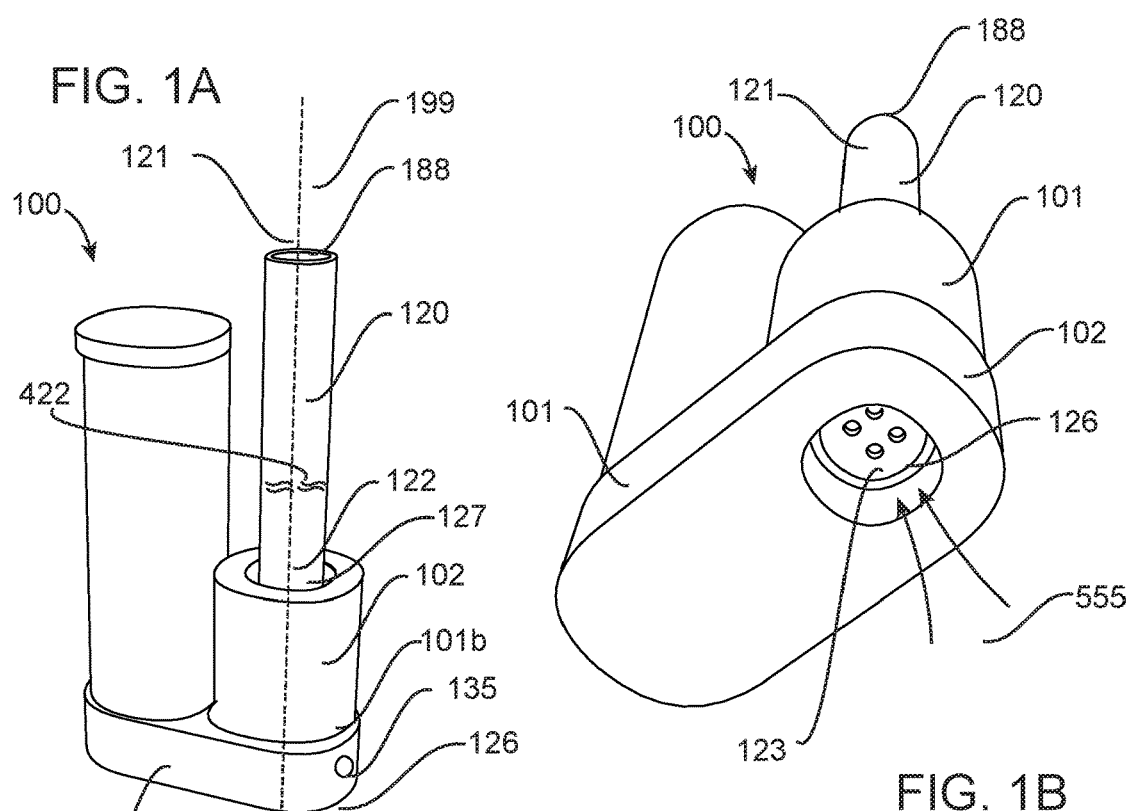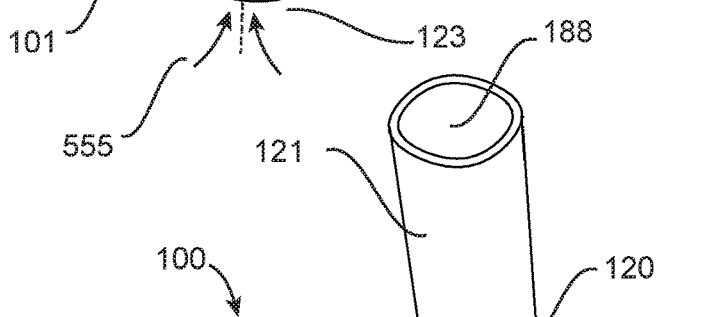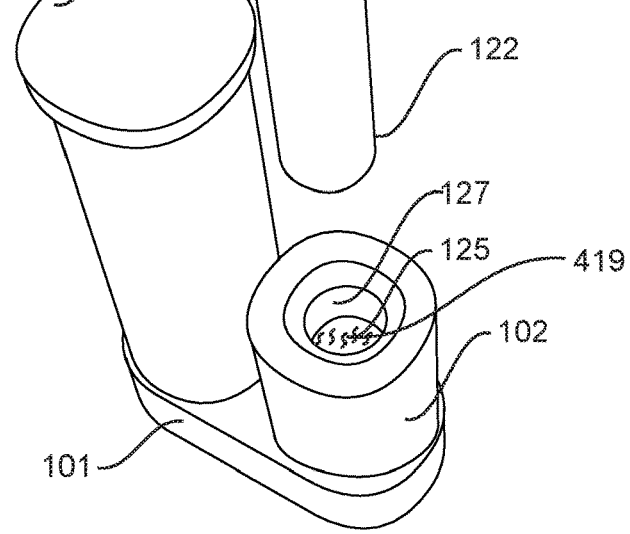

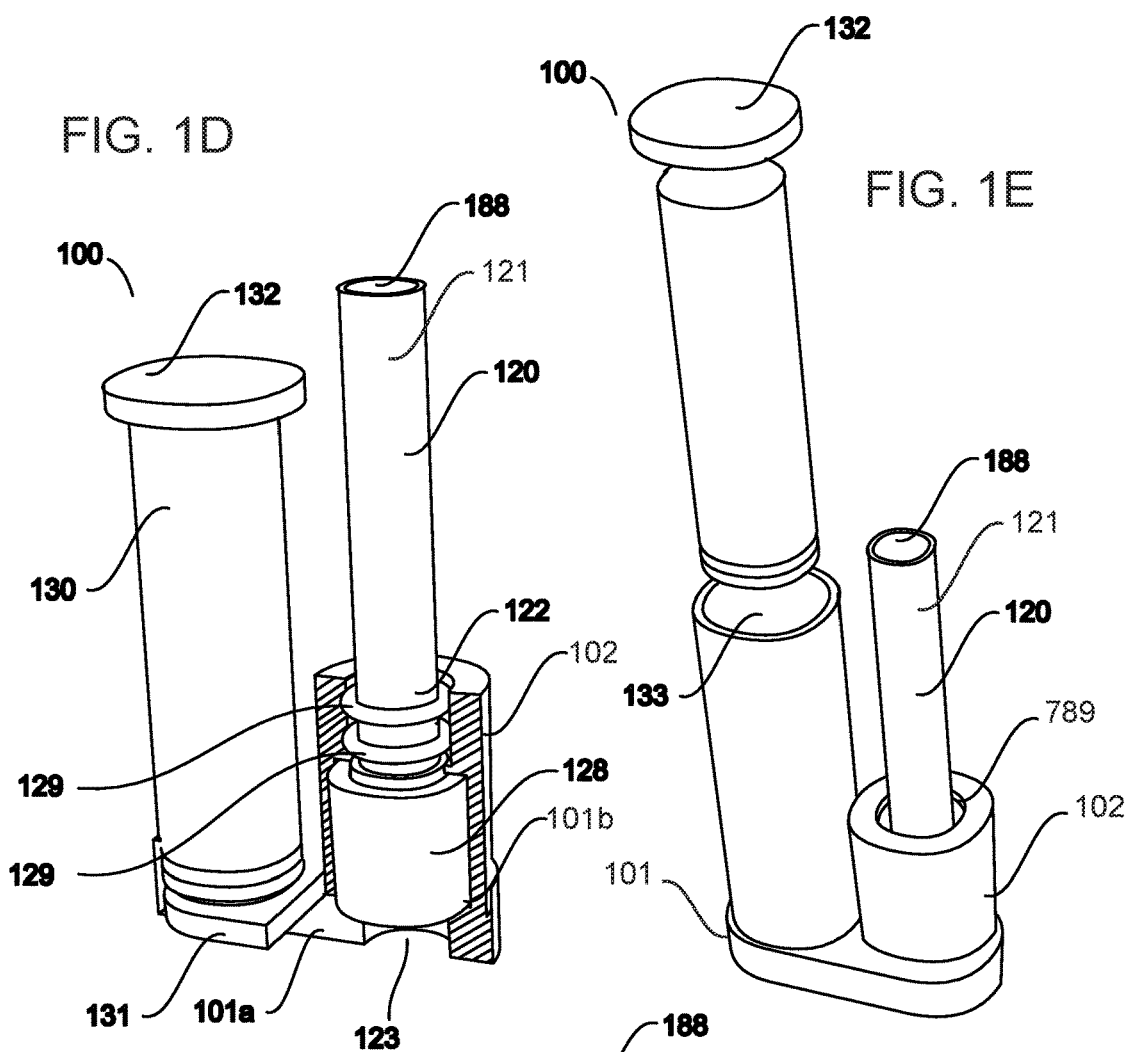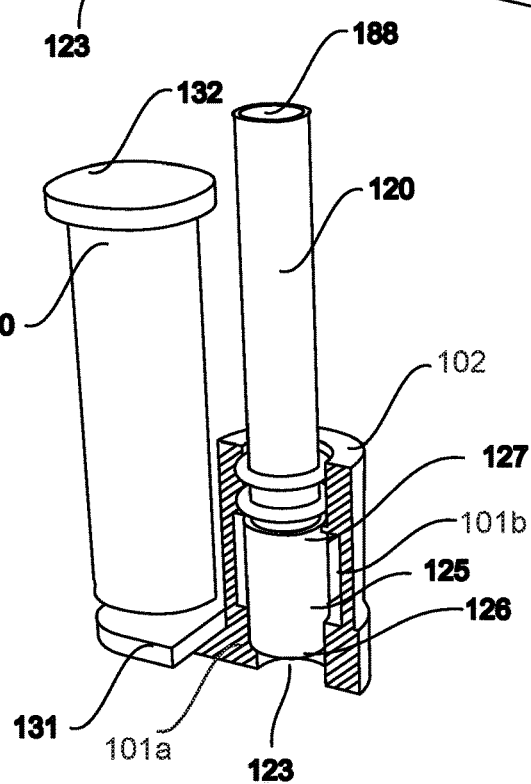

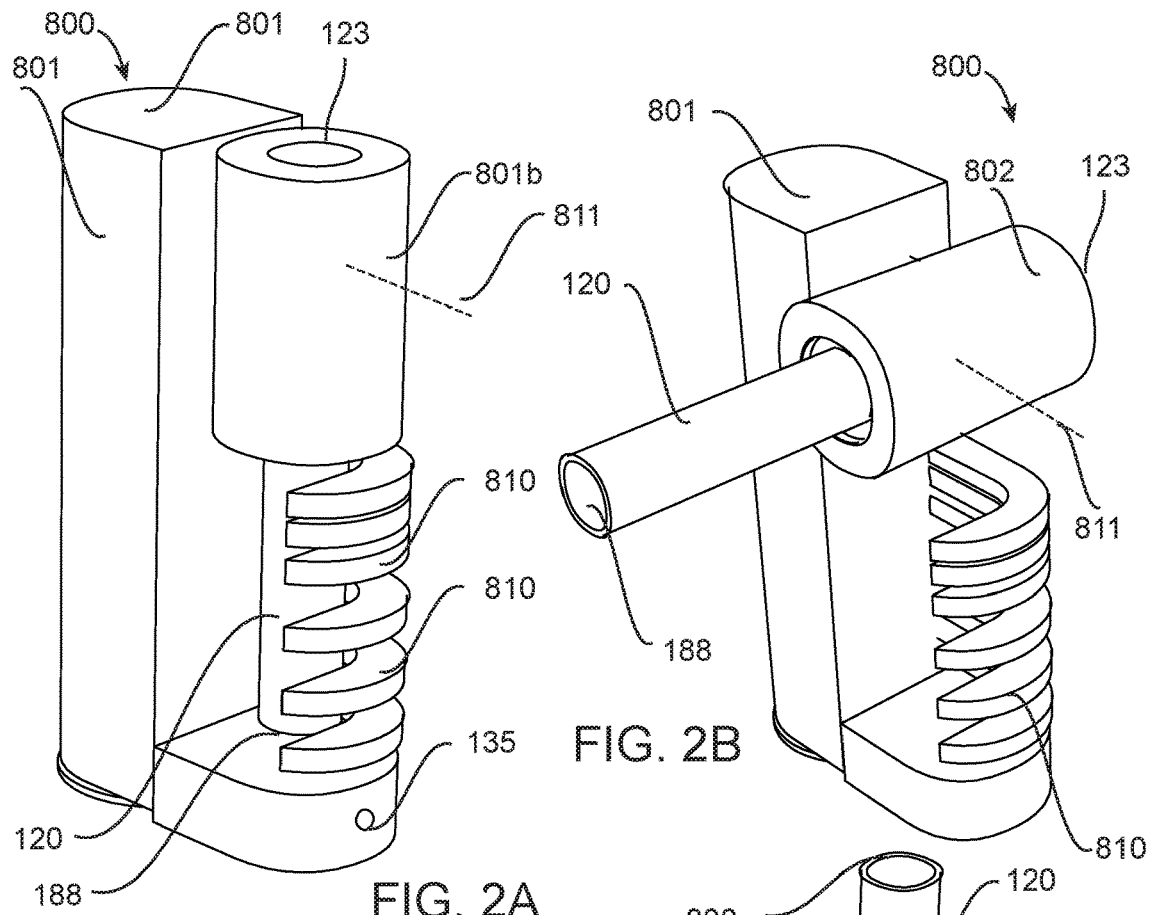
FIG. 2A
FIG. 2B
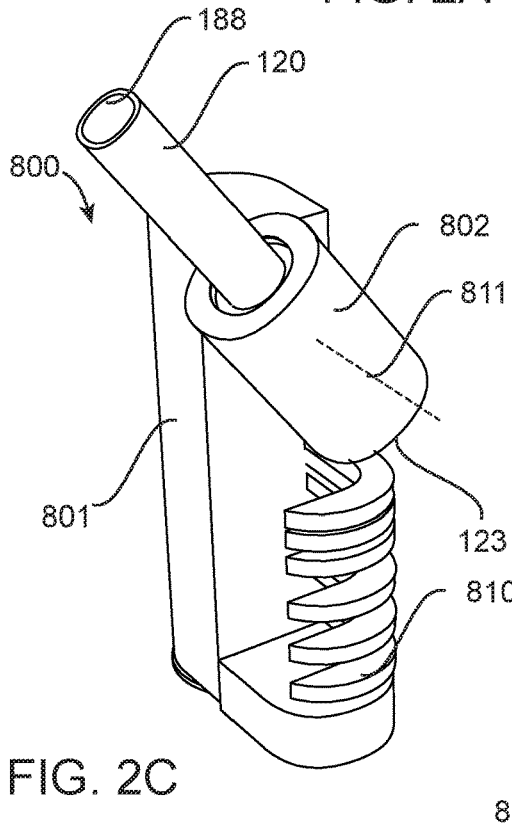
FIG. 2C
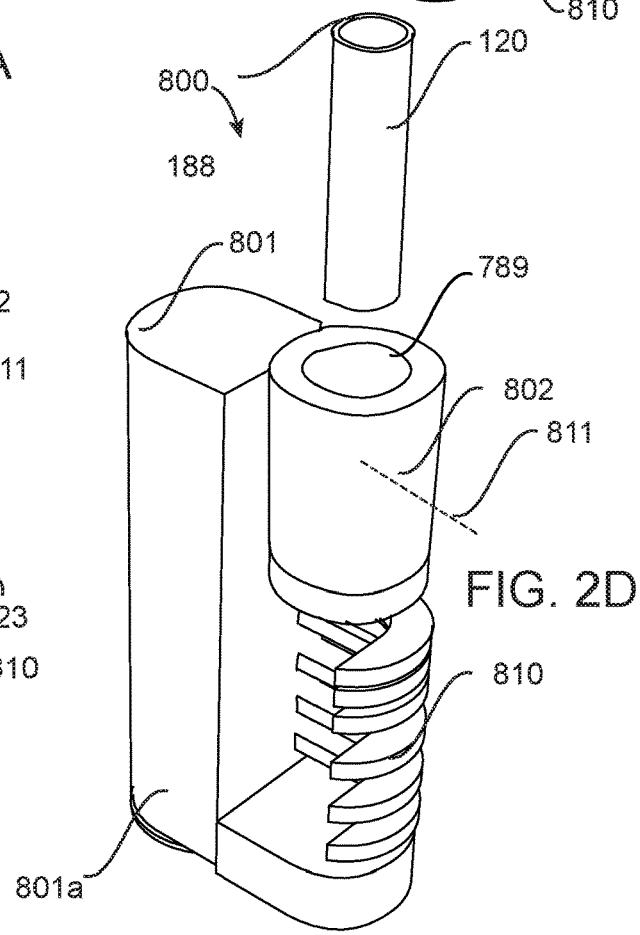
FIG. 2D

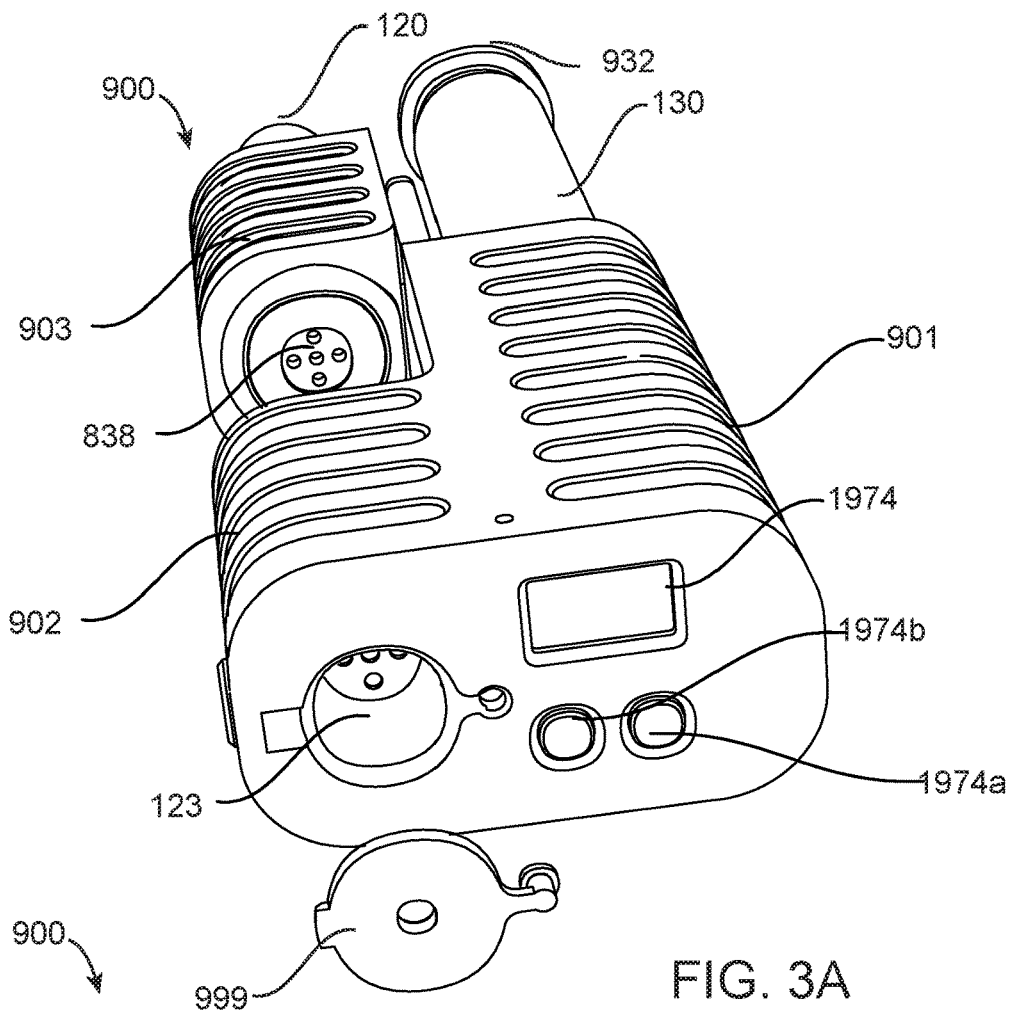
FIG. 3A
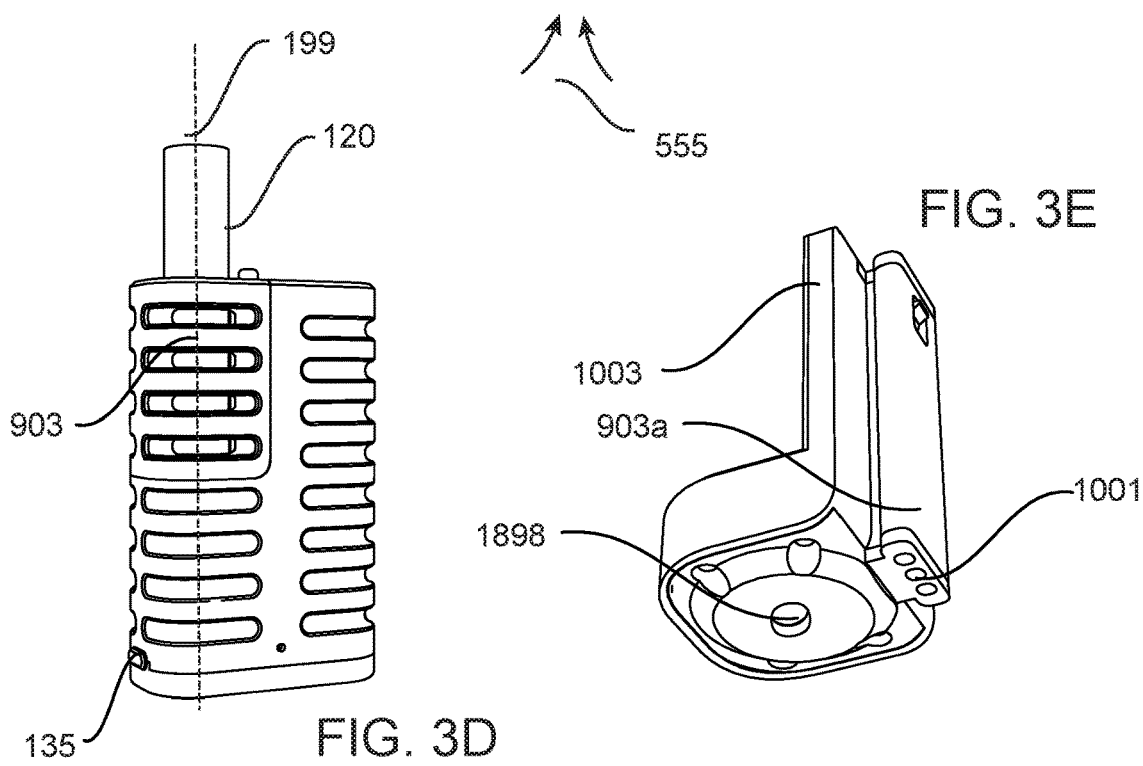
FIG. 3D
FIG. 3E

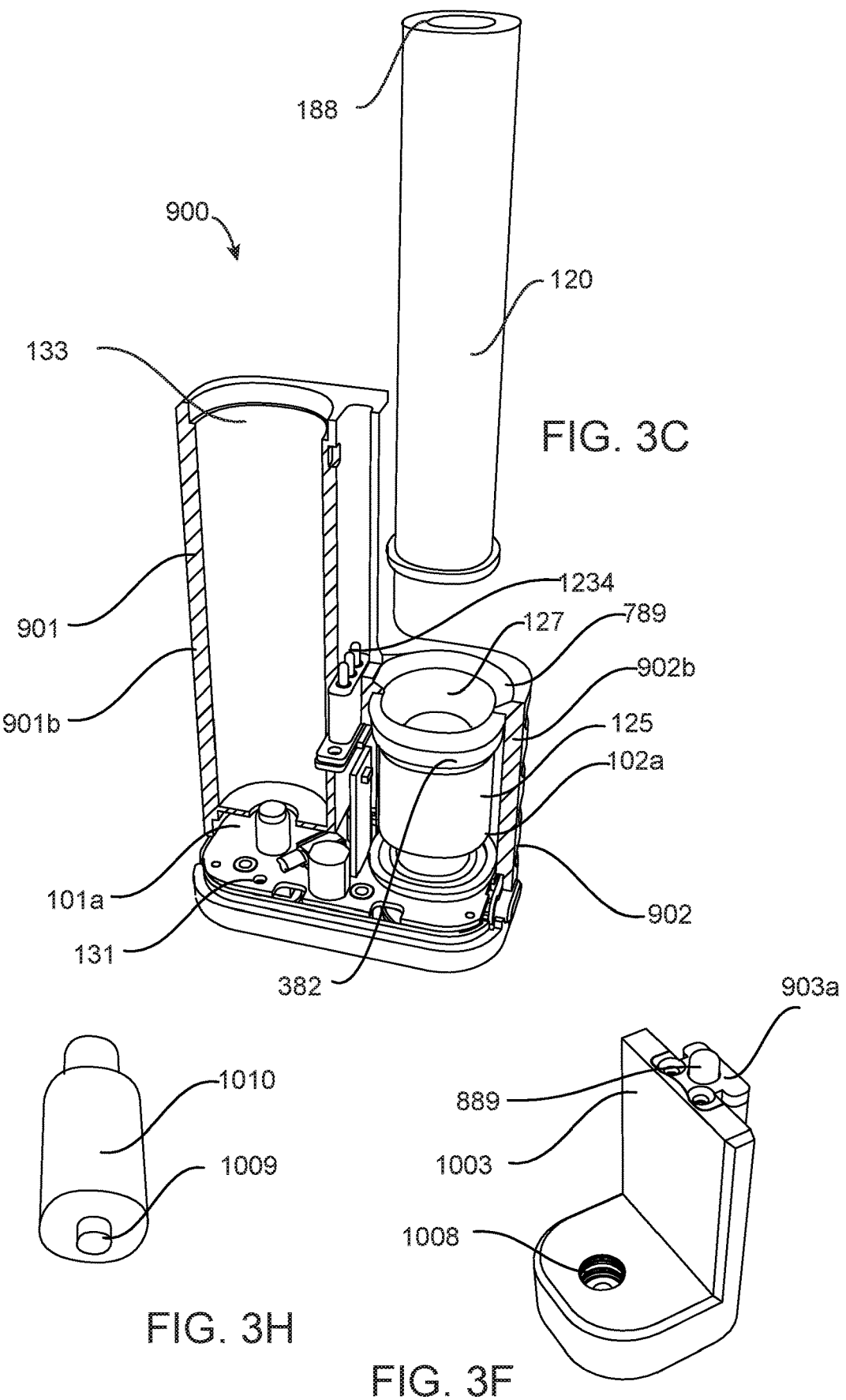

AROMATHERAPY VAPORIZATION DEVICE

CROSS REFERENCE TO RELATED APPLICATION

This application is a continuation of U.S. patent application Ser. No. 15/372,308, filed Dec. 7, 2016, which claims priority from U.S. Provisional Applications 62/263,751 filed on Dec. 7, 2015, the entire contents of each of which are incorporated herein by reference.

TECHNICAL FIELD OF THE INVENTION

The technical field relates to a device for vaporization of phyto materials and more specifically to a device for aromatherapy vaporization.

BACKGROUND OF THE INVENTION

Aromatherapy generally uses essential oils, which are extracted from phyto materials, such as leaves of plants, for therapeutic benefits. These essential oils are either massaged into the skin or can be inhaled. In some cases, the phyto materials are heated in order to release the essential oils therefrom. By heating these phyto materials at predetermined temperatures, essential oils and extracts are boiled off, depending upon the temperature at which these phyto materials are heated, an aroma or vapor is given off, which is then inhaled by a user for its therapeutic benefits. Devices that provide such operation are generally known as vaporizers. Different phyto materials release vapors at different temperatures. Some release vapors at 120 degrees Celsius, whereas others at 220 degrees Celsius. Ideally, the predetermined temperature is less than a combustion temperature of the phyto material or loose-leaf material.

Many aromatherapy vaporization devices on the market utilize a heating chamber in order to heat leaf material in order to vaporize its contents so that desired oils and other flavor materials can be separated from the leaf material in order to be consumed by a user of the device in a vaporized form.

Many vaporization device on the market that are in the prior art have air entering the heating chamber that flows in proximity to electrical components, such as the control circuits, printed circuit boards (PCB) and also that flows into the heating chamber from within the housing. This air entering the heating chamber is therefore usually flavored by the components over which it passes. For example, when the electrical components within a vaporizer housing are getting hot and air passes over them, the heat emitted from these components will tend to taint flavor in a negative way. For a vaporizer to offer maximum flavor, it is preferably to have the air enter the heating chamber, the incoming air, not from within the vaporizer housing, not having it contact electrical components and not having it contact heated PCBs.

Additionally, components such as rubber and other elastomers in proximity of the heating chamber will also adversely affect the flavor of the air incoming to the heating chamber as well as the flavor of the vapor and hot air mixture. Furthermore, with many of these prior art vaporizers, phyto material may leak from the heating chamber into the housing and requires disassembly of the housing in order to facilitate cleaning, where in some cases many of these devices are not made to be disassembled and as such the phyto material cannot be cleaned therefrom.

It is therefore an object of the invention to provide an aromatherapy vaporization device that overcomes the aforementioned deficiencies.

SUMMARY

In accordance with the embodiments of the invention there is provided an aromatherapy vaporization device comprising: a first housing having a first housing inside surface and a first housing outside surface, a second housing coupled with the first housing, and having a second housing inside surface and second housing outside surface, the first and second housing outside surfaces forming a substantial enclosure for enclosing the first and second housing inside surfaces, the second housing comprising: a heating chamber disposed proximate the second housing inside surface having an upstream ambient air input port disposed proximate a first end thereof and protruding through the second housing outside surface, the upstream ambient air input port in fluid communication for receiving of ambient air and the heating chamber having a heating chamber second end downstream of the first end, the heating chamber second end forming an aperture within the second housing outside surface; an inhalation tube having an inhalation tube second end releasably and fluidly coupled with the heating chamber second end downstream thereof and having an inhalation tube first end downstream of the inhalation tube second end and terminating at an inhalation aperture in fluid communication therewith, in a second mode of operation a continuous fluid pathway formed from the upstream ambient air input port through the heating chamber from the heating chamber first end to the heating chamber second end and the inhalation tube and terminating at the inhalation aperture; a battery compartment disposed within the first housing having a battery compartment lid, the battery compartment for removably receiving of a battery; a control circuit disposed within the first housing and proximate the first housing inside surface and electrically coupled with the battery and electrically coupled with the heating chamber and electrically coupled with a switch, wherein the aromatherapy vaporization device is for operating in a first mode of operation and the second mode of operation, in a first mode of operation the aromatherapy vaporization device is for having the inhalation tube uncoupled from the first housing and for having phyto material inserted into the heating chamber and having an other than continuous fluid pathway formed from the downstream ambient air input port to the inhalation aperture, in the second mode of operation the inhalation tube being coupled with the first housing and for the switch being actuated and the control circuit for providing of electrical current from the battery to the heating chamber for heating of the phyto material disposed therein to a predetermined temperature for creating of phyto material vapor to be emitted therefrom, the phyto material vapor for mixing with ambient air received upstream of the heating chamber within the heating chamber and within the inhalation tube for being inhaled from the inhalation aperture by a user, wherein the ambient air when entering the upstream ambient air input port does not contact the control circuit and first housing inside surface and the second housing inside surface and contacts at least one of the first housing outside surface and the second housing outside surface.

In accordance with the embodiments of the invention there is provided an aromatherapy vaporization device comprising: a first housing having a first housing inside surface and a first housing outside surface, a second housing coupled with the first housing and having a second housing inside surface and second housing outside surface, the first and second housing outside surfaces forming a substantial enclosure for enclosing the first and second housing inside surfaces, the second housing comprising: a heating chamber disposed proximate the second housing inside surface having an upstream ambient air input port disposed proximate a first end thereof and protruding through the second housing outside surface, the upstream ambient air input port in fluid communication for receiving of ambient air and the heating chamber having a heating chamber second end downstream of the first end, the heating chamber second end forming an aperture within the second housing outside surface; an inhalation tube having an inhalation tube second end releasably and fluidly coupled with the heating chamber second end downstream thereof and having an inhalation tube first end downstream of the inhalation tube second end and terminating at an inhalation aperture in fluid communication therewith, the heating chamber second end forming an aperture within the second housing outside surface; a continuous fluid pathway formed from the upstream ambient air input port through the heating chamber from the heating chamber first end to the heating chamber second end and the inhalation tube and terminating at the inhalation aperture in a second mode of operation; a battery compartment disposed within the first housing having a battery compartment lid, the battery compartment for removably receiving of a battery; a control circuit disposed within the first housing and proximate the first housing inside surface and electrically coupled with the battery and electrically coupled with the heating chamber and electrically coupled with a switch; a set of protective ribs coupled with the first housing; a pivot axis perpendicular to the inhalation tube for rotatably coupling of the second housing to the first housing, the pivot axis for allowing of the second housing to rotate up to degrees in relation to the first housing about the pivot axis, wherein the aromatherapy vaporization device is for operating in a first mode of operation and the second mode of operation, in a first mode of operation the aromatherapy vaporization for having the inhalation tube uncoupled from the first housing and for having phyto material inserted into the heating chamber and having an other than continuous fluid pathway formed from the upstream ambient air input port to the inhalation aperture, in the second mode of operation the inhalation tube being coupled with the first housing and for the switch being actuated and the control circuit for providing of electrical current from the battery to the heating chamber for heating of the phyto material disposed therein to a predetermined temperature for creating of phyto material vapor to be emitted therefrom, the phyto material vapor for mixing with ambient air received upstream of the heating chamber within the heating chamber and within the inhalation tube for being inhaled from the inhalation aperture by a user, wherein the ambient air when entering the upstream ambient air input port does not contact the control circuit and first housing inside surface and the second housing inside surface and contacts at least one of the first housing outside surface and the second housing outside surface, wherein in the first mode of operation and the second mode of operation the second housing is rotated between approximately 90 degrees and 180 degrees along the pivot axis and in a third mode of operation the angle of the pivot axis is approximately zero degrees and the inhalation tube is substantially recessed within the set of protective ribs.

In accordance with the embodiments of the invention there is provided an aromatherapy vaporization device comprising: a first housing having a first housing inside surface and a first housing outside surface, a second housing coupled with the first housing, and having a second housing inside surface and second housing outside surface, the first and second housing outside surfaces forming a substantial enclosure for enclosing the first and second housing inside surfaces, the second housing comprising: a heating chamber disposed proximate the second housing inside surface having an upstream ambient air input port disposed proximate a first end thereof and protruding through the second housing outside surface, the upstream ambient air input port in fluid communication for receiving of ambient air and the heating chamber having a heating chamber second end downstream of the first end, the heating chamber second end forming an aperture within the second housing outside surface; a fourth housing comprising a set of electrical contacts and having an atomizer air input port for being fluidly coupled with the heating chamber second end and having a female threaded coupling for engaging an atomizer male threaded coupling; a battery compartment disposed within the first housing having a battery compartment lid, the battery compartment for removably receiving of a battery; a control circuit disposed within the first housing and proximate the first housing inside surface and electrically coupled with the battery and electrically coupled with the heating chamber and electrically coupled with a switch; control buttons and electrically coupled with the control circuit; a set of electrical pins protruding past the second housing outside surface and electrically coupled with the control circuit and for electrically engaging the set of electrical contacts as part of the fourth housing; a continuous fluid pathway formed from the upstream ambient air input port through the heating chamber from the heating chamber first end to the heating chamber second end and through to the atomizer air input port and through the male and female threaded coupling and terminating at the inhalation aperture in a second mode of operation, wherein in a fifth mode of operation electrical power from the battery is provided to the atomizer and not to the heating chamber without activating of the switch, wherein in a first mode of operation the for having the fourth housing uncoupled from the first housing and for having phyto material inserted into the heating chamber and having an other than continuous fluid pathway formed from the upstream ambient air input port to the inhalation aperture, in the second mode of operation the atomizer is coupled with the fourth housing and for the switch being actuated and the control circuit for providing of electrical current from the battery to the atomizer and to the heating chamber for heating of the phyto material disposed therein to a predetermined temperature for creating of phyto material vapor to be emitted therefrom, the phyto material vapor for mixing with ambient air received upstream of the heating chamber within the heating chamber and together propagating through the atomizer for being inhaled from the inhalation aperture, where the control buttons are used to toggle operation between the second and fifth modes of operation, wherein the ambient air when entering the upstream ambient air input port does not contact the control circuit and first housing inside surface and the second housing inside surface and contacts at least one of the first housing outside surface and the second housing outside surface.

BRIEF DESCRIPTION OF THE DRAWINGS

FIG. 1A illustrates an aromatherapy vaporization device in accordance with a first embodiment of the invention;

FIG. 1B illustrates an aromatherapy vaporization device in accordance with a first embodiment of the invention and showing shows an upstream ambient air input port;

FIG. 1C illustrates An aromatherapy vaporization device in accordance with a first embodiment of the invention and in a first mode of operation;

FIG. 1D illustrates a cutaway view and showing a control circuit and an inside surface of the first housing;

FIG. 1E illustrates removal of a battery from a battery compartment;

FIG. 1F illustrates a cutaway view of the first and second housing and reveals a heating chamber;

FIG. 2A illustrates an aromatherapy vaporization device in accordance with a second embodiment of the invention with a pivot axis at zero degrees and the aromatherapy vaporization device is in a third mode of operation;

FIG. 2B illustrates an aromatherapy vaporization device in accordance with a second embodiment of the invention with a pivot axis angle at ninety degrees and the aromatherapy vaporization device is in a second mode of operation;

FIG. 2C illustrates an aromatherapy vaporization device in accordance with a second embodiment of the invention with a pivot axis angle is at approximately one hundred thirty five degrees and the aromatherapy vaporization device is in a second mode of operation;

FIG. 2D illustrates an aromatherapy vaporization device in accordance with a second embodiment of the invention with a pivot axis having an angle of approximately one hundred eighty degrees and the aromatherapy vaporization device is in a first mode of operation;

FIG. 3A illustrates an aromatherapy vaporization device in accordance with a third embodiment of the invention and it includes a removable one way airflow valve;

FIG. 3C illustrates a cutaway view of the aromatherapy vaporization device showing the control circuit and the first housing inside surface and the second housing inside surface;

FIG. 3D illustrates a third embodiment the invention showing a continuous fluid pathway;

FIG. 3E illustrates a fourth housing from a bottom perspective with a set of electrical contacts visible;

FIG. 3F shows a fourth housing from a top perspective view where a female threaded coupling is shown;

FIG. 3H illustrates a standard 5 mm thread atomizer for being coupled with the fourth housing.

DETAILED DESCRIPTION OF EMBODIMENTS OF THE INVENTION

Figure 2E:
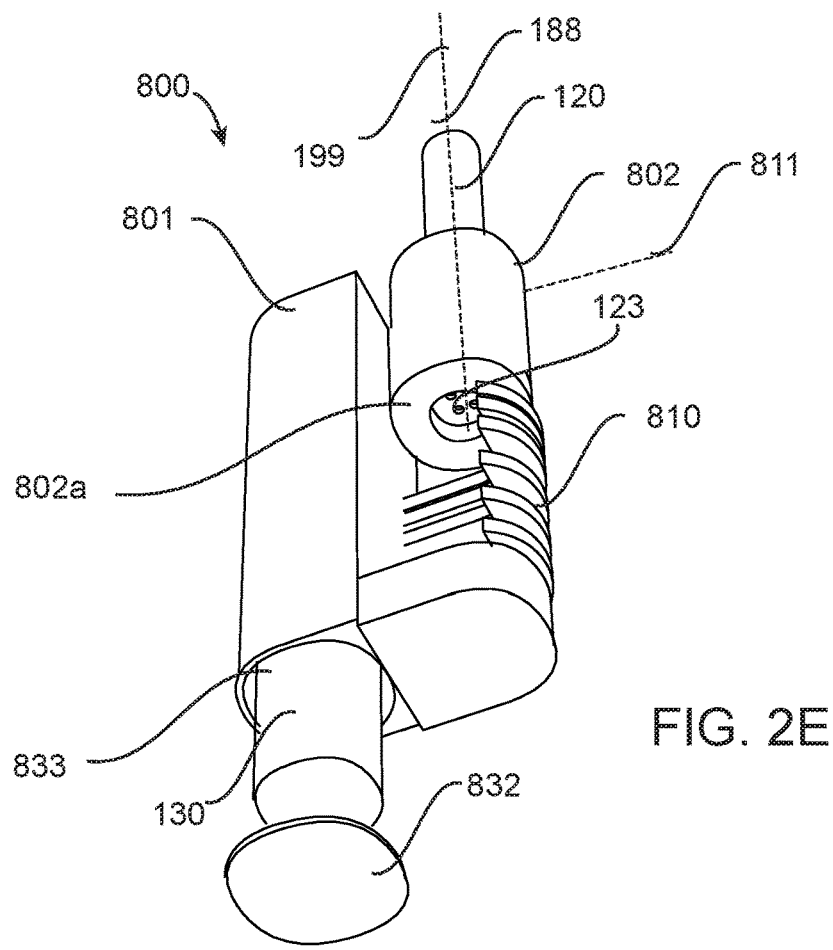
FIG. 2E illustrates a removal of a battery from a battery compartment of the aromatherapy vaporization device.

FIGS. 1A, 1B, and 1C illustrate an aromatherapy vaporization device (AVD) 100 in accordance with a first embodiment of the invention. FIG. 1B illustrates the AVD 100 in showing an upstream ambient air input port 123 and FIG. 1C illustrates the AVD 100 in a first mode of operation. FIG. 1D illustrates a cutaway view and showing a control circuit and an inside surface of the first housing.

As is shown in FIG. 1A, the AVD 100 comprises a first housing 101 having a first housing inside surface 101a (shown in FIG. 1D) and a first housing outside surface 101b and a second housing 102 having a second housing inside surface 102a and a second housing outside surface 102b. The second housing 102 is coupled with the first housing 101 and first and second housing outside surfaces 101b and 102b forming an enclosure for enclosing of the first and second housing inside surfaces 101a and 102a.

The second housing comprising a heating chamber 125 (FIG. 1C) disposed therein and proximate the second housing inside surface 102a, the heating chamber having an upstream ambient air input port 123 (FIG. 1B) disposed proximate a first end thereof 126 and protruding through the second housing outside surface 102b, the upstream ambient air input port 123 in fluid communication for receiving of ambient air 555, the heating chamber having a heating chamber second end 127 (FIG. 1C) downstream of the first end 126.

As is shown in FIG. 1A, an inhalation tube 120 is provided having an inhalation tube second end 122 releasably and fluidly coupled with the heating chamber second end 127 downstream thereof and having an inhalation tube first end 121 downstream of the inhalation tube second end 122 and terminating at an inhalation aperture 188 in fluid communication therewith.

A continuous fluid pathway 199 is formed from the upstream ambient air input port 123 through the heating chamber first end 126 and through to the heating chamber second end 127 and inhalation tube 120 and terminating at the inhalation aperture 188. The heating chamber second end 127 forming an aperture 789 within the second housing outside surface 102b (FIG. 1E).

A battery compartment 133 (FIG. 1E) is provided having a battery compartment lid 132, the battery compartment 133 for removably receiving of a battery 130. A control circuit 131 electrically coupled with the battery 130 and electrically coupled with the heating chamber 125 and electrically coupled with a switch 135. Preferably, the battery 130 is a rechargeable battery, such as an 18650, 3300 mAh, lithium ion battery as is known to those of skill in the art.

Referring to FIGS. 1C and 1A, the AVD 100 is for operating in a first mode of operation (FIG. 1C) and a second mode of operation (FIG. 1A), in the first mode of operation the AVD 100 for having the inhalation tube 120 uncoupled from the first housing 101 and for having phyto material 419 inserted into the heating chamber 125, in the second mode of operation (FIG. 1A) the inhalation tube 120 for being coupled with the first housing 101 and the switch 135 for being actuated and the control circuit 131 for providing of electrical current from the battery 130 to the heating chamber 125 for heating of the phyto material 419 disposed therein to a predetermined temperature for creating of phyto material vapor 422 therefrom, the phyto material vapor 422 for mixing with ambient air 555 within the heating chamber 125 and within the inhalation tube 120 for being inhaled from the inhalation aperture 188 by a user, wherein the ambient air 555 when entering the upstream ambient air input port 123 does not contact the control circuit 131 and the first housing inside surface 101a and the second housing inside surface 101a and contacts the first and second housing outside surface 101b and 102b.

Preferably, the inhalation tube 120 is made from glass as this offers a cleaner taste, although ceramic material is also envisaged. Preferably, the heating chamber 125 comprising a conductive ceramic heating element although a conductive metal heating element is also envisaged. Optionally the heating chamber 125 comprises a convection heating chamber for heating of the phyto material using hot air to heat it to the predetermined temperature. Preferably, the predetermined temperature is between 380 degrees Fahrenheit and 420 degrees Fahrenheit.

Preferably, a silicone ring 129 is used for frictionally engaging the inhalation tube 120 with the second housing 101. Preferably, the silicone ring is a high temperature silicone ring.

FIG. 1D illustrates a thermal insulating layer 128 disposed about the heating chamber 125 and this results in minimal thermal coupling between the first housing 101 and the heating chamber 125 is shown. This assembly facilitates maintaining of heat inside the heating chamber as well as for having minimal transfer of thermal energy from heating chamber 125 to the first and second housing 101 and 102.

Figure 1G:
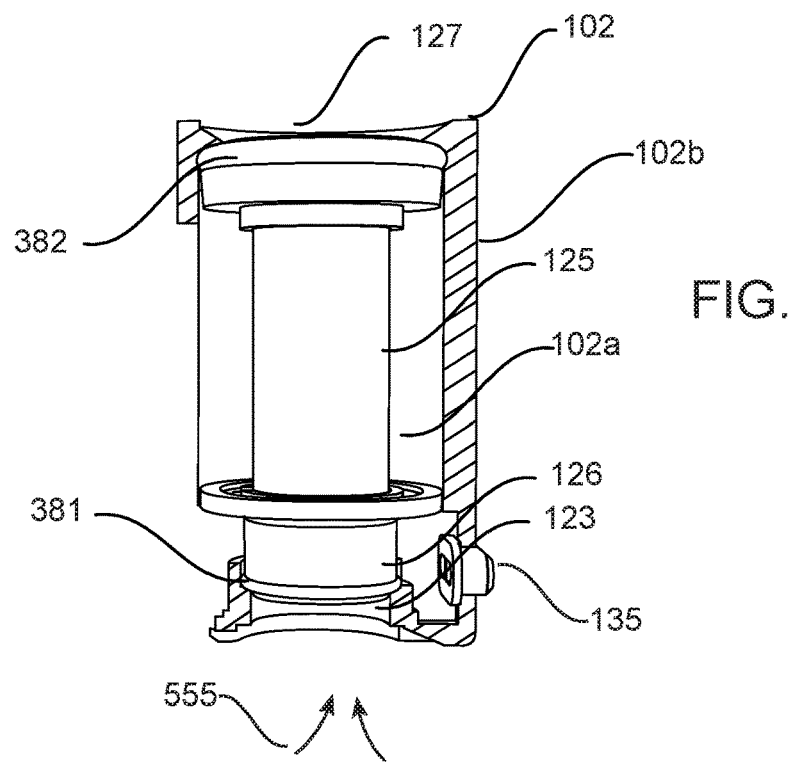
FIG. 1G illustrates a heating chamber and the first and second housings in detail with the inside surfaces thereof being more evident.

Additionally, the first housing inside surface 101a faces the control circuit 131 as is shown in FIG. 1F. FIG. 1G illustrates a cutaway view of the second housing 102 having a second housing inside surface 102a and second housing outside surface 102b with the control circuit and the battery compartment and the first housing inside surface 101a and a first housing outside surface 101b removed for clarity. A first sealing ring 381 and a second sealing ring 382 are disposed between the heating chamber 125 first and second end 126 and 127 and the second housing inside surface 102a, the sealing rings 381 and 382 substantially prevent air that is between the heating chamber 127 and the second housing inside surface 102a and the first housing inside surface 102a from being mixed with the ambient air 555 when entering the heating chamber 125 through the upstream ambient air input port 123. The first sealing ring 381 and the second sealing ring 382 frictionally engage the second housing inside surface 102a.

FIG. 1E shows the battery 130 being removed from the battery compartment 133 through uncoupling of the battery compartment lid 132 from the first housing 101. FIG. 1F illustrates the heating chamber 125 without the thermal insulating layer 128 disposed around.

FIGS. 2A through 2E illustrate the AVD 800 in accordance with a second embodiment of the invention. Referring to FIG. 2A, the AVD 800 is formed from a first housing 801 having a first housing inside surface 101a (FIG. 1F) and a first housing outside surface 801b. A second housing 802 having a second housing inside surface 102a and second housing outside surface 802b. An upstream ambient air input port 123 is disposed proximate a first end thereof 126, the upstream ambient air input port 123 in fluid communication for receiving of ambient air 555, the heating chamber 125 having a heating chamber second end 127 downstream of the first end 126.

Referring to FIG. 2B, an inhalation tube 120 having an inhalation tube second end 122 releasably and fluidly coupled with the heating chamber second end 127 downstream thereof and having an inhalation tube first end 121 downstream of the inhalation tube second end 122 and terminating at an inhalation aperture 188 in fluid communication therewith.

A continuous fluid pathway 199 formed from the upstream ambient air input port 123 through the heating chamber 125 and inhalation tube 120 and terminating at the inhalation aperture 188.

Referring to FIG. 2E, the first housing 801 comprising a battery compartment 833 having a battery compartment lid 832, the battery compartment 833 for removably receiving of a battery 130 and a control circuit 131 (not shown) (FIG. 1F) electrically coupled with the battery 130 and electrically coupled with the heating chamber 125 and electrically coupled with a switch 135. The switch 135 for being actuated and the control circuit 131 providing of electrical current from the battery 130 to the heating chamber 125 for heating of the phyto material 419 disposed therein to a predetermined temperature for creating of phyto material vapor 422 therefrom. A set of protective ribs 810 are coupled with the first housing 801.

A pivot axis 811 for coupling of the second housing 802 to the first housing 801, the pivot axis 811 for allowing of the second housing to pivot up to 180 degrees in relation to the first housing 180.

The AVD 800 is for operating the first mode of operation (FIG. 2D) and the second mode of operation (FIG. 2B, 2C). Wherein in the first mode of operation and the second mode of operation the second housing 802 is rotated between approximately 90 degrees and 180 degrees about the pivot axis 811 and in a third mode of operation (FIG. 2A) the angle of the pivot axis 811 is approximately zero degrees and the inhalation tube 120 is recessed within the set of protective ribs 810. Preferably, the protective ribs 810 substantially enclose the inhalation tube 120 and prevent it from being damaged in a situation when the AVD 800 is dropped for example.

FIG. 3A illustrates an AVD 900 in accordance with a third embodiment of the invention. The AVD 900 includes a removable one way airflow valve 999 fluidly coupled with the upstream ambient air input port 123 for receiving of ambient air 555 and for allowing of the ambient air 555 to pass through the valve 999 in a substantially single direction and to not allow the ambient air 555 and phyto material vapor 422 to exit from the heating chamber 125. This advantageously allows for the phyto material vapor 422 to remain within the heating chamber for a longer time and results in a larger dose when inhaled from the inhalation aperture 188. In this figure the removable one way airflow valve 999 is shown uncoupled from the second housing 902.

Figure 3B:
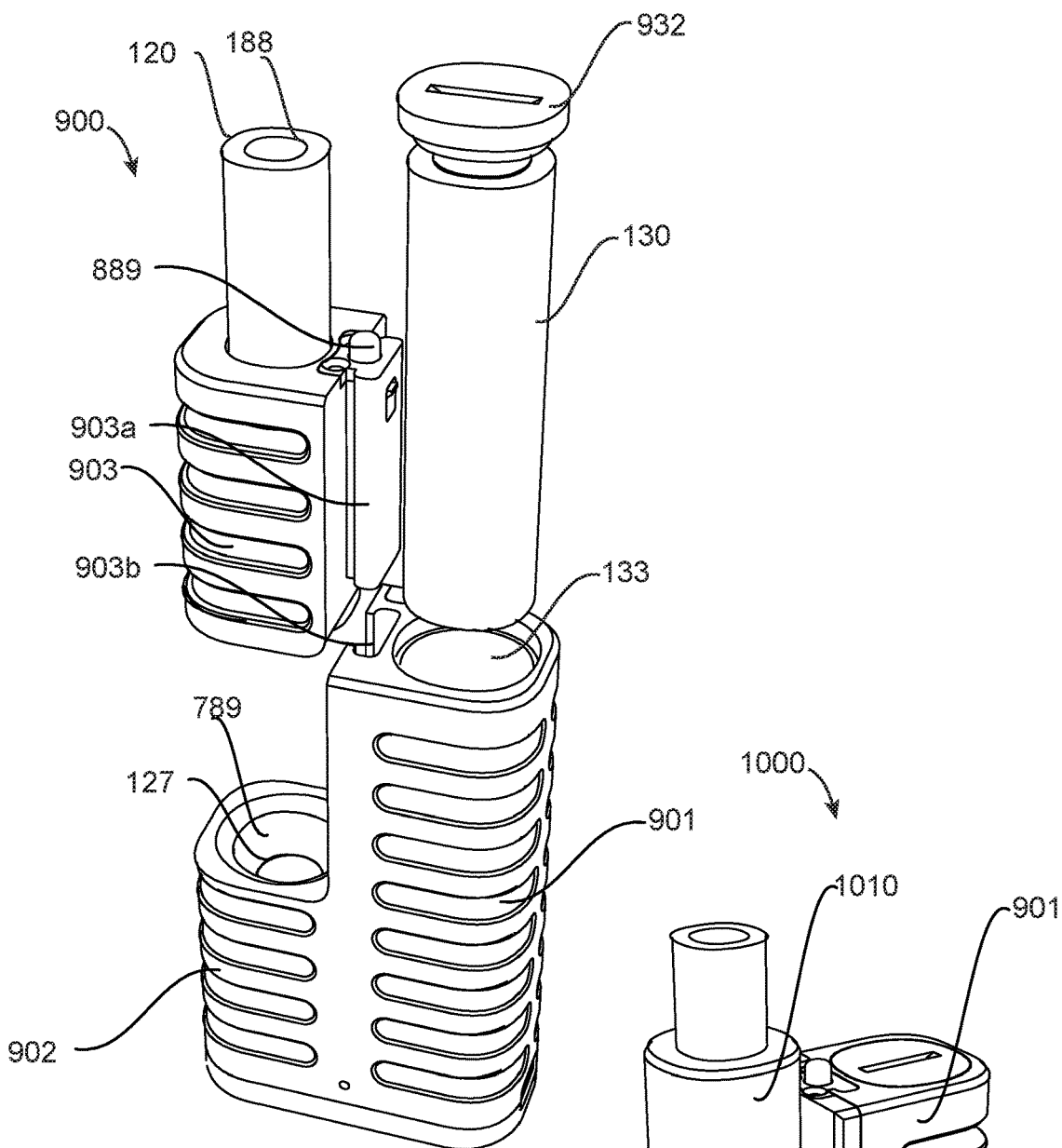
FIG. 3B illustrates the aromatherapy vaporization device in the first mode of operation from a perspective view with the battery compartment opened and battery being removed therefrom.

FIG. 3B illustrates the AVD 900 in the first mode of operation from a perspective view with the battery compartment 133 opened and the battery shown 130 being removed therefrom. FIG. 3C illustrates a cutaway view of the AVD 900 showing the control circuit 131 and the first housing inside surface 101a and the second housing inside surface 102a.

Referring to FIG. 3C, a cutaway view of the first and second housing 901 and 902 of the DFV 900 is shown. The AVD 900 comprises a first housing 901 having a first housing inside surface 101a and a first housing outside surface 901b and a second housing 902 having a second housing inside surface 102a and a second housing outside surface 902b. The second housing 902 comprising a heating chamber 125 (FIG. 3C) disposed therein and proximate the second housing inside surface 102a, the heating chamber having an upstream ambient air input port 123 (FIG. 1A) disposed proximate a first end thereof 126 and protruding through the second housing outside surface 902b, the upstream ambient air input port 123 in fluid communication for receiving of ambient air 555, the heating chamber having a heating chamber second end 127 (FIG. 1C) downstream of the first end 126.

As is shown in FIG. 3A, the inhalation tube 120 is provided having an inhalation tube second end 122 releasably and fluidly coupled with the heating chamber second end 127 downstream thereof and having an inhalation tube first end 121 downstream of the inhalation tube second end 122 and terminating at an inhalation aperture 188 in fluid communication therewith. The inhalation tube 120 is releasably coupled with a third housing 903, wherein the third housing 903 comprises a slide 903a formed as a part thereof and the first housing has a track 903b formed as a part thereof for engaging of the slide 903a. This facilitates sliding of the third housing 903 to allow the inhalation tube 120 second end 121 to be releasably and fluidly coupled with the heating chamber second end 127 in the second mode of operation and for sliding of the third housing 903 slide 903a out of the track 903b for facilitating loading of the phyto material into the heating chamber 125 in the first mode of operation. A locking mechanism 889 is also provided for facilitating locking of the third housing 903 with respect to the first housing 901 in the second mode of operation. The locking mechanism is preferably a spring locking mechanism whereby the spring is depressed to facilitate unlocking of the third housing 903 with respect to the first housing 901. In addition as is shown in FIG. 3A, a display screen 1974 is provided and electrically coupled with the control circuit 131, the digital display screen for displaying the predetermined temperature. Control buttons 1974a and 1974b are provided for increasing and decreasing the predetermined temperature.

Referring to FIG. 3D, an accordance with the third embodiment of the DFV 900, a continuous fluid pathway 199 is formed from the upstream ambient air input port 123 through the heating chamber first end 126 and through to the heating chamber second end 127 and inhalation tube 120 and terminating at the inhalation aperture 188.

Referring to FIG. 3B, a battery compartment 133 is provided having a battery compartment lid 132, the battery compartment 133 for removably receiving of an energy storage member such as battery 130. Referring to FIG. 3C, a control circuit 131 electrically coupled with the battery 130 and electrically coupled with the heating chamber 125 and electrically coupled with a switch 135. The switch 135 for being actuated and the control circuit 131 providing of electrical current from the battery 130 to the heating chamber 125 for heating of the phyto material 419 disposed therein to a predetermined temperature for creating of phyto material vapor 422 therefrom.

As is shown in FIG. 3A, a mesh 838 is provided proximate the heating chamber second end 127. This mesh 838 facilitates phyto material 419 from exiting the heating chamber 125 second 127. Preferably, this mesh 838 is made from glass, although metal is also envisaged.

Referring to FIG. 3C, the first housing inside surface 101a faces the control circuit 131 and the second housing inside surface 102a faces the heating chamber 125. The first sealing ring 381 (FIG. 1G) and a second sealing ring 382 are disposed between the heating chamber 125 first and second end 126 and 127 and the second housing inside surface 102a, the sealing rings 381 and 382 substantially prevent air that is between the heating chamber 127 and the second housing inside surface 102a and the first housing inside surface 102a from being mixed with the ambient air 555 when entering the heating chamber 125 through the upstream ambient air input port 123. The first sealing ring 381 and the second sealing ring 382 frictionally engage the second housing inside surface 102a.

Also visible in FIG. 3C are a set of electrical pins 1234 protruding past the second housing outside surface 902b and electrically coupled with the control circuit 131 for electrically engaging a set of electrical contacts 1001 disposed as part of the fourth housing 1003 in accordance with a fourth embodiment of the invention of the DFV 1000. The fourth housing 1003 is shown in more detail in FIGS. 3E and 3F. FIG. 3E shows the fourth housing 1003 from a bottom perspective view where the set of electrical contacts 1001 are visible. FIG. 3F shows the fourth housing 1003 from a top perspective view where a female threaded coupling 1008 is shown.

Figure 3G:
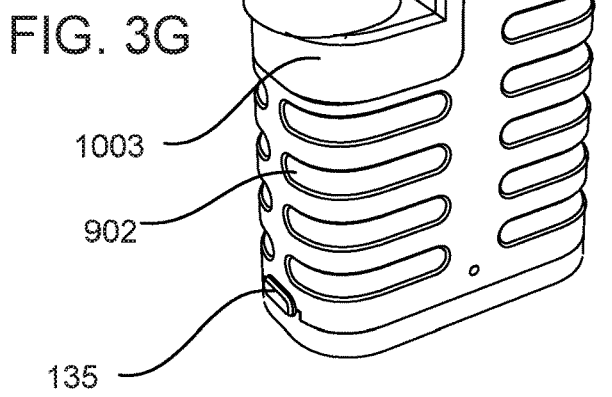
FIG. 3G illustrates the fourth embodiment of the invention having a standard atomizer attached to the fourth housing.

FIG. 3G illustrates a version of the atomizer 1010 or cartomizer or clearomizer attached to the fourth housing 1003, where such an atomizer 1010 has a male 5 mm threaded coupling 1009, as is known to the persons skilled in the art. Through the mechanical and electrical coupling of the atomizer 1010 with the female threaded coupling 1008 and through the electrical coupling of the set of electrical pins 1234 with the set of electrical contacts 1001, the control circuit 131 provides electrical power to the atomizer 1010 as opposed to the heating chamber 125 in a fifth mode of operation. Through the female and male threaded coupling 1008 and 1009, both electrical current and air flow. In this manner, the operation of the heating chamber 125 is optionally disabled and the operation of the atomizer 1010 is enabled in the fifth mode of operation. Atomizers 1010 are known in the art for receiving of liquids or oils and for heating them to release a vapor therefrom. When the heating chamber is disabled then ambient air flows from the upstream ambient air input port 123 and into an atomizer ambient air input port 1898 (FIG. 3E) from the heating chamber second 127 and through the heating chamber into the atomizer 1010 for inhalation from the inhalation aperture 188. When the heating chamber 125 operation is enabled, then ambient air 555 flows into the heating chamber 125 from the upstream ambient input port 123 and mixes with phyto material vapors for propagating through the atomizer 1010 for inhalation through the inhalation aperture 188.

Control buttons 1974a and 1974b coupled with the control circuit 131 are provided for increasing and decreasing the predetermined temperature as well as in combination for triggering operation of the DFV 1000 between the second mode of operation and the fifth mode of operation. In addition, the control buttons 1974a and 1974b are utilized for setting a wattage that is provided for the atomizer from the battery 130.

Advantageously the AVD in accordance with the embodiments of the invention is easy to clean as the residue from the vaporization process and phyto material 419 that has been vaporized is easily removed from the heating chamber as well as proximate the upstream ambient air input port 123 and does not fall between the first and second housing inside surfaces 101a and 102a and the control circuit 131 and the heating chamber 125 as is found in many prior art devices.

Additionally ambient air 555 entering the heating chamber through the doesn't have adverse flavors associated with it as it doesn't pass into the heating chamber 125 from within the first and second housing of the DFV in accordance with the embodiments of the invention and as such the first housing inside surface 101a and the second housing inside surface 102a and air flowing over hot electrical components and PCBs. Furthermore, because the heating chamber has its upstream ambient air input port 123 exposed to the outside, any residue left inside the heating chamber can easily fall into the ambient air and not into the internal components of the AVD. Furthermore, hot electrical components and PCBs also potentially cause harm as they release toxic chemicals and these are not meant to be inhaled as they may potentially cause harm to an end user. Ambient air entering the heating chamber does not flow past the hot electrical components and PCBs.

Having the battery removable allows the end user to be able to change the battery when the electrical power is low and the user can optionally carry spare batteries. Further advantageously, having the fourth housing 1003 as part of the fourth embodiment of the invention 1000 allows for the DFV to also be used with existing atomizer modules, which then provides for a dual use device where the user can enjoy the DFV in accordance with the first through third embodiments of the invention with phyto materials and the fourth embodiment of the invention with phyto material extracts that are at times packaged within these atomizers 1010.

Numerous other embodiments are envisaged without departing from the spirit or scope of the invention.

What I claim is:

1. An aromatherapy vaporization device comprising:
   a device housing comprising a housing outer surface and a housing inner surface;
   a heating chamber surrounded by the housing inner surface, the heating chamber defining a phyto material receiving volume between a first end and a second end of the heating chamber;
   an ambient air input port formed proximate a first end of the device housing and proximate the first end of the heating chamber, the ambient air input port fluidly coupled to the phyto material receiving volume and the ambient air input port being positioned to intake ambient air from external to the device housing;
   an energy storage member disposed within the device housing and surrounded by the housing inner surface;
   a control circuit disposed within the device housing and surrounded by the housing inner surface, the control circuit coupled to the energy storage member and to the heating chamber;
   an inhalation conduit extending between an upstream conduit end and a downstream conduit end, wherein an inhalation aperture is defined at the downstream conduit end, and the upstream conduit end is fluidly connected to the phyto material receiving volume;
   wherein phyto material is receivable in the phyto material receiving volume through the second end of the heating chamber;
   wherein a continuous fluid pathway is defined between an upstream pathway end positioned at the ambient air input port and a downstream pathway end positioned at the inhalation aperture, the continuous fluid pathway extending through the phyto material receiving volume, the continuous fluid pathway being a sealed pathway that prevents the control circuit, the energy storage member and the housing inner surface from contacting any fluid that passes through the continuous fluid pathway;
   wherein the energy storage member controllably supplies power to the heating chamber;
   wherein the heating chamber is operable to heat the phyto material received within the phyto material receiving volume to a predetermined vaporization temperature to generate phyto material vapor;
   wherein, in response to inhalation from the inhalation aperture by a user, the phyto material vapour mixes with the ambient air drawn through the phyto material receiving volume thereby creating a mixture of phyto material vapour and ambient air drawn through the inhalation conduit to the inhalation aperture; and
   wherein the ambient air is drawn into the phyto material receiving volume through the ambient air input port and through the continuous fluid pathway.

2. The aromatherapy vaporization device according to claim 1 comprising:
   at least one sealing ring disposed proximate the heating chamber first end, the at least one sealing ring operable to substantially prevent air that is between the heating chamber and the housing inner surface from mixing with the ambient air as the ambient air enters the heating chamber through the ambient air input port, wherein the at least one sealing ring frictionally engages the housing inner surface.

3. The aromatherapy vaporization device according to claim 2, wherein
   the at least one sealing ring comprises a first sealing ring and a second sealing ring.

4. The aromatherapy vaporization device according to claim 1 comprising:
   a silicone ring disposed proximate the heating chamber second end, the silicone ring sealing the inhalation conduit upstream conduit end with the heating chamber second end.

5. The aromatherapy vaporization device according to claim 1 comprising: a removable one way airflow valve fluidly coupled with the ambient air input port, wherein the one way airflow valve permits the ambient air to pass into the heating chamber in a first direction, and prevents the mixture of phyto material vapour and ambient air from exiting the heating chamber in a direction opposite the first direction.

6. The aromatherapy vaporization device according to claim 1 comprising:
   an additional housing having a slide located on an exterior surface thereof;
   a track located on the housing outer surface, the track being engageable with the slide of the additional housing; and
   wherein sliding the additional housing relative to the device housing allows the upstream conduit end of the inhalation conduit to be one of fluidly coupled and fluidly uncoupled with the heating chamber second end.

7. The aromatherapy vaporization device according to claim 1 comprising:
   a mesh proximate the second end of the heating chamber for facilitating a reduction in phyto material traveling from the phyto material receiving volume into the inhalation conduit.

8. The aromatherapy vaporization device according to claim 1, wherein the heating chamber comprises a phyto material receiving surface, an open end, and at least one sidewall that together define the phyto material receiving volume, and the upstream conduit end is detachably attachable to the open end of the heating chamber.

9. The aromatherapy vaporization device according to claim 8, wherein the inhalation conduit comprises a sealing member proximate the upstream conduit end, wherein the sealing member frictionally engages one of the housing outer and inner surfaces while the upstream conduit end is attached to the open end of the heating chamber.

10. The aromatherapy vaporization device according to claim 1, wherein the heating chamber comprises a conductive heating element, and wherein the predetermined temperature is between 380 degrees Fahrenheit and 420 degrees Fahrenheit.

11. The aromatherapy vaporization device according to claim 1, wherein the heating chamber comprises a convection heating chamber for heating the phyto material to the predetermined temperature with hot air, and wherein the predetermined temperature is between 380 degrees Fahrenheit and 420 degrees Fahrenheit.

12. An aromatherapy vaporization device comprising:
a device housing comprising a first housing section and a second housing section, the second housing section having a second housing inner surface, the first housing section having a first housing inner surface;
an atomizer comprising a heating chamber and a phyto material receiving volume, the heating chamber disposed within the second housing section with the second housing inner surface surrounding the heating chamber and located proximate the phyto material receiving volume;
an energy storage member disposed within the first housing section;
a control circuit disposed within the first housing section, the control circuit coupled to the energy storage member;
a female threaded coupling disposed as part of the first housing section engageable with a male threaded coupling disposed as part of the second housing section, while engaged the male and female threaded couplings forming a mechanical and electrical coupling of the atomizer for the control circuit operable to control a supply of power from the energy storage member to the heating chamber through the mechanical and electrical coupling of the atomizer;
an ambient air input port provided in the second housing section, the ambient air input port fluidly coupled to the heating chamber proximate the phyto material receiving volume;
an inhalation conduit extending between an upstream conduit end and a downstream conduit end, wherein an inhalation aperture is defined at the downstream conduit end, and the upstream conduit end is fluidly connectable to the heating chamber within the second housing section;
wherein the heating chamber is operable to heat phyto material extract received within the phyto material receiving volume to a predetermined vaporization temperature to generate phyto material vapor;
wherein, while the upstream conduit end is fluidly connected to the ambient air input port, a continuous fluid pathway is defined between an upstream pathway end positioned at the ambient air input port and a downstream pathway end positioned at the inhalation aperture,
the continuous fluid pathway extending through the heating chamber so that when the phyto material extract is heated to the predetermined vaporization temperature and a user inhales from the inhalation aperture, i) ambient air is drawn into the heating chamber, ii) the ambient air mixes with the phyto material vapor, and iii) the mixed ambient air and phyto material vapor is drawn through the inhalation conduit to the inhalation aperture; and
wherein the continuous fluid pathway is sealed from the first housing inner surface such that the ambient air drawn in from the ambient air input port is prevented from contacting any one of the control circuit and the energy storage member of the first housing section, and the ambient air is drawn into the heating chamber through the upstream conduit end fluidly connectable to the heating chamber within the second housing section.

13. The aromatherapy vaporization device according to claim 12 comprising: at least one a control button coupled with the control circuit for controlling a power wattage delivered from the energy storage member to the atomizer.

14. The aromatherapy vaporization device according to claim 12, wherein the heating chamber comprises a conductive heating element and is for receiving a leaf material, and wherein the predetermined temperature is between 380 degrees Fahrenheit and 420 degrees Fahrenheit.

15. The aromatherapy vaporization device according to claim 12, wherein the phyto material receiving volume comprises a phyto material extract receiving volume for receiving phyto material extract.

16. The aromatherapy vaporization device according to claim 12, wherein the inhalation conduit comprises a sealing member proximate the upstream conduit end, wherein the sealing member frictionally engages one of the housing outer and inner surfaces while the upstream conduit end is attached to an open end of the heating chamber.

17. The aromatherapy vaporization device according to claim 16 comprising at least a first sealing ring and a second sealing ring disposed between heating chamber first and second ends and the second housing inside surface, the first and second sealing rings operable to substantially prevent air that is between the heating chamber and the second housing inside surface and the first housing inside surface from mixing with the ambient air as the ambient air enters the heating chamber through the ambient air input port, wherein at least one of the first sealing ring and the second sealing ring frictionally engage the second housing inside surface.

18. The aromatherapy vaporization device according to claim 17 comprising: a mesh proximate the second end of the heating chamber for facilitating a reduction in phyto material extract traveling from the phyto material receiving volume into the inhalation conduit.

19. The aromatherapy vaporization device according to claim 12 comprising:
a one way airflow valve fluidly coupled with the ambient air input port, wherein the one way airflow valve permits the ambient air to pass into the heating chamber in a first direction, and prevents the mixed ambient air and phyto material vapor from exiting the heating chamber in a direction opposite the first direction.

20. The aromatherapy vaporization device according to claim 12, wherein the inhalation conduit is releasably fluidly connectable to the heating chamber within the second housing section and wherein the inhalation conduit is uncoupled from the second housing section for one of having phyto material extract inserted into the heating chamber and for having phyto material extract removed from the heating chamber such that an other than continuous fluid pathway is formed between the ambient air input port and the inhalation aperture.

* * * * *